(12) United States Patent
Spaide (10) Patent No.: US 8,287,560 B2
(45) Date of Patent: Oct. 16, 2012

(54) SHARP TROCHAR FOR INSERTION OF A CANNULA IN VITRECTOMY SURGERY

(76) Inventor: Richard Spaide, New York, NY (US)

(*) Notice: Subject to any disclaimer, the term of this patent is extended or adjusted under 35 U.S.C. 154(b) by 0 days.

(21) Appl. No.: 11/754,637

(22) Filed: May 29, 2007

(65) Prior Publication Data

US 2008/0021399 A1    Jan. 24, 2008

Related U.S. Application Data

(60) Provisional application No. 60/820,976, filed on Aug. 1, 2006, provisional application No. 60/823,913, filed on Aug. 30, 2006, provisional application No. 60/832,194, filed on Jul. 19, 2006.

(51) Int. Cl.
*A61B 17/34* (2006.01)
(52) U.S. Cl. ......................................... 606/185; 606/166
(58) Field of Classification Search .................. 606/107, 606/166, 167, 170, 185–189, 223; 600/180; 604/264, 272; D24/112, 130

See application file for complete search history.

(56) References Cited

U.S. PATENT DOCUMENTS

| | | | | |
|---|---|---|---|---|
| 4,177,814 A | * | 12/1979 | Knepshield et al. | 604/26 |
| 5,215,526 A | * | 6/1993 | Deniega et al. | 604/164.09 |
| 5,389,077 A | * | 2/1995 | Melinyshyn et al. | 604/117 |
| 5,397,335 A | * | 3/1995 | Gresl et al. | 606/185 |
| 7,645,286 B2 | * | 1/2010 | Catanese et al. | 606/151 |
| 2002/0013597 A1 | * | 1/2002 | McFarlane | 606/185 |
| 2002/0141904 A1 | * | 10/2002 | Rosen et al. | 422/102 |
| 2006/0135973 A1 | * | 6/2006 | Hawkins et al. | 606/167 |

* cited by examiner

*Primary Examiner* — Ryan Severson
(74) *Attorney, Agent, or Firm* — Ronald Abramson; Hughes Hubbard & Reed LLP (57) ABSTRACT

A system of instruments is provided for vitrectomy surgery, comprising a sharp trochar, a cannula and a cannula valve cap. The sharp trochar provided also has applicability to other fields of surgery. The sharp trochar has a hollow-ground blade that reduces the force necessary for insertion and upon removal leaves a wound with improved healing characteristics. The trochar is selectably insertable in a cannula, and in a preferred embodiment the cannula and the trochar are adapted with mutually tapered exterior surfaces to as to define a smooth transition in diameter to further facilitate insertion. A sealing valve cap is also provided for the cannula, designed to provide sealing while reducing the force required in for inserting instruments into the cannula. A method for angled insertion of this assembly is also disclosed.

8 Claims, 10 Drawing Sheets

SHARP TROCHAR FOR INSERTION OF A CANNULA IN VITRECTOMY SURGERY

CROSS-REFERENCE TO RELATED APPLICATIONS

This application claims the benefit of U.S. Provisional Application No. 60/820,976 ("New Sharp Trochar for Vitrectomy Surgery"), filed Aug. 1, 2006, and U.S. Provisional Application No. 60/823,913 ("Biplanar Sharp Trochar for Vitrectomy Surgery"), filed Aug. 30, 2006, and U.S. Provisional Application No. 60/832,194 ("Cannula Valve Cap for Vitrectomy Surgery"), filed Jul. 19, 2006. The entire disclosures of each of said provisional applications are hereby respectively incorporated herein by reference.

BACKGROUND OF THE INVENTION

1. Field of the Invention

The Invention is in the field of surgical instruments, and more specifically concerns a system of instruments for vitrectomy surgery, comprising a sharp trochar, a cannula and a cannula valve cap. The sharp trochar provided also has applicability to other fields of surgery.

2. Background of the Related Art

Vitrectomy surgery, particularly small incision vitrectomy surgery, is done using a cannula to hold open the incision into the eye. A cannula may be introduced with a trochar (sometimes spelled "trocar"), which is slidably inserted into the cannula. The incision is made in the sclera (wall of the eye) with the trochar, and the cannula is installed in the sclera by sliding out the trochar. The cannula is then used to insert and remove other instruments during the surgical procedure. These components can be adapted to be used together as a system of surgical instruments.

Trochars, alone or in combination with cannulae, are used in many types of surgery, in addition to vitrectomy surgery, with variations in size and features as required by the particular type of surgery involved. They are used in such applications in order to introduce cannulae, and other such instruments as well, into blood vessels or body cavities. Examples of types of surgery in which trochars are used include cardiovascular and laparoscopic surgery, in addition to ophthalmic surgery.

Conventionally, a trochar is often made by grinding a straight tapered edge at the distal end of a piece of metal wire or tubing, so that the straight tapered edge produces a sharp tip at the distal end of the trochar. A typical prior art trochar (not including the attached handle or boss) is shown in FIG. 1A. The trochar 101 has a straight tapered edge 102 starting at a first point 105 and an ending at tip 106. The tapered edge 102 has a straight line contour, so that, in side view, the tapered blade section of the trochar 101 resembles a wedge and is much like that found on a hypodermic needle. In a top view, also shown in FIG. 1A, edge 102 is seen as an oval shape.

As shown, for example, in Chen et al., U.S. Pat. Pub. No. 2006/0089526 ("Chen"), and illustrated in FIG. 1B herein, trochar 101 may coupled with a cannula 121, in such a way that the trochar is slidably inserted through the tubular body 122 of the cannula, and that the tapered edge 102 of the tapered blade section of the trochar 101 extends past tubular body 122. A boss or handle 124 may be used to hold the trochar and cannula assembly. The trochar 101 is then introduced to the sclera and initially the tip at the end 106 of the tapered edge 102 cuts into the eye. The exterior side 103 of the trochar opposite the tapered edge has the round shape of a cylinder. As the tapered edge 102 of the trochar is pushed into the eye, the incision into the sclera expands until the tapered edge completely enters the eye. The shaft of the trochar, along with the slightly wider tubular body of the cannula, is then also pushed into the eye, until the wider top section 123 of the cannula 121 is resting on the surface of the sclera. The trochar 101 is then withdrawn from the eye, leaving the cannula 121 in place. The cannula then holds the incision open, and the tubular body of the cannula functions as a conduit for the passage of various types of surgical instruments into the eye. A valve cap 125 also may be inserted into the cannula prior to insertion, and the trochar inserted through the valve cap, with the valve cap being left in place after removal of the trochar to prevent the free flow of fluids in the absence of an instrument being positioned within the cannula.

There are shortcomings associated with each of the prior art components currently available for use in such a system of instruments.

First, insertion of a prior art trochar and cannula combination causes substantial plastic deformation of the sclera tissue to accommodate the shaft of the trochar and the tubular body 122 of the cannula, leaving a smile-shaped wound 140 as shown in FIG. 1C. Such a wound does not appose or heal well. Thus, the field currently lacks a trochar designed to minimize the stretching of the sclera tissue and the force necessary to insert the trochar, and at the same time create an incision that is shaped to promote rapid healing.

Figure 1:
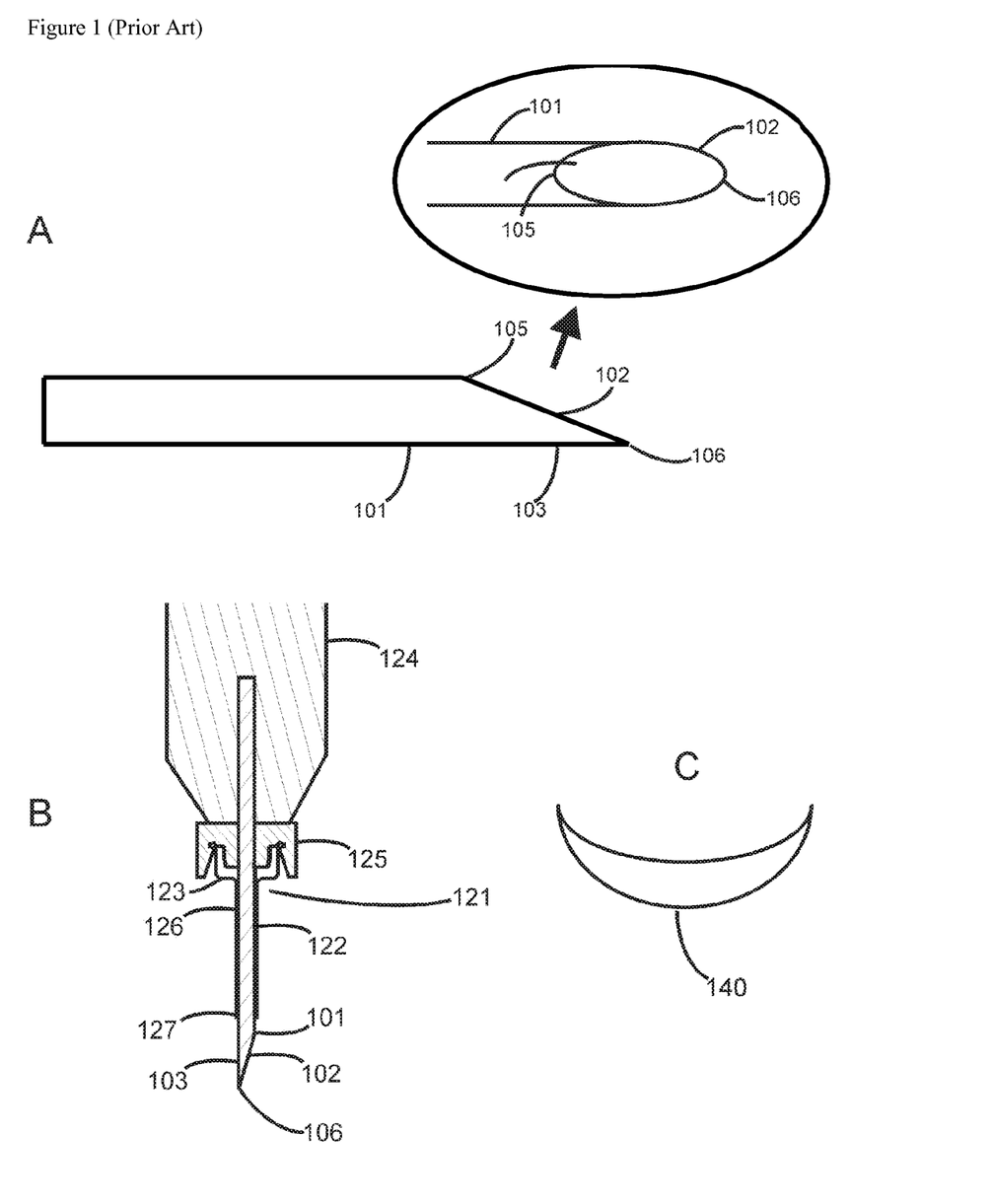
FIG. 1A is a side sectional view of the blade section of a prior art trochar.
FIG. 1B is a side sectional view of an assembly as used in the prior art comprising a trochar, a cannula and a cannula cap.
FIG. 1C is a drawing schematically illustrating a wound left on the sclera after the use of apparatus such as that shown in FIG. 1B.

Chen shows two variations upon the prior art trochar. In one variation, the sharp point of the trochar is created by grinding one angled edge entirely across the shaft of the trochar and then sharpening the point with two smaller surfaces, resulting in an off-center tip and two sharp edges. In another variation, the sharp point of the trochar is created by grinding three angled edges onto the shaft of the trochar, resulting in an on-center tip with three sharp edges. According to Chen, the two-edged embodiment of his trochar has the disadvantage of requiring more surgical force than the three-edged embodiment. However, neither embodiment creates a wound that seals particularly well, with the three-edged embodiment being the inferior of the two designs in this regard, because it creates a triradiate incision in which the wound-closing force from the wall of the eye is not perpendicular to any axis of the incision. While smaller incisions, such as for 25 gauge surgery, may not leak much after surgery because the vitreous can occlude the open wound, better wound creation strategies need to be employed for larger incisions. Similarly, with regard to the cannula, as seen in FIG. 1 of Chen, the distal end 16 of the cannula has a flat transverse cut at the distal end of its tubular sleeve member 20 (at 127 as shown in FIG. 1B herein), creating a discontinuity of diameter with the shaft of the trochar upon which it is to be disposed, resulting in an impediment to smooth insertion.

There is a free passage 126 through the cannula 121 allowing intraocular fluid out of the eye. It is desirable to be able to control the flow of such fluid when removing or changing instruments. However, current cannula caps, such as valve cap 125 in FIG. 1B, while providing a basic sealing function, do not have features to facilitate ease of insertion and removal of instruments. First, the opening provided is very small, making the insertion of a flexible instrument, such as soft-tipped insertion cannula, nearly impossible. The area provided for insertion must be reduced because it must fit into the "passageway" that is part of Chen's valve cap structure, thereby providing only for a very small opening, which would bend any flexible instrument instead of allowing it to penetrate the small opening. Second, Chen's valve cap is provided with an unbroken septum, recessed within an internal passageway in the cap of the cannula, where the septum is cut during insertion and forms flaps which are relied upon for sealing. This also results in a smaller opening for insertion of instruments, and unpredictable slit configurations, not optimized for reducing the force necessary to insert and withdraw an instrument. Third, there is no way to get rid of the valve mechanism in Chen's design if the needs of surgery dictate its removal.

SUMMARY OF THE INVENTION

The present invention provides a system of instruments that are preferably coordinated in design so as to interoperate, which facilitates improved surgical procedures and provides solutions for the problems that have arisen with the prior art components.

In one embodiment, the present invention provides a trochar with a tapered blade section having a concave contour. Instead of a wedge-shaped tapered section of the prior art where the taper is in a straight line, the trochar in accordance with the present invention has a tapered contour having a concave shape with respect to an imaginary linear line drawn between the start point and the end point of the tapered contour. The curved geometry of a tapered blade section contour as used in that embodiment results in the front portion of the blade being sharper and having a smaller profile, thereby promoting cutting of the tissue to initiate and expand the incision, and reducing the stretching of the tissue, thus overcoming the shortcomings of the wedge-shaped blade contours of the prior art.

There is also provided a cannula with a tapered tubular sleeve member to ease insertion into the sclera. A corresponding taper on the shaft of one embodiment of a trochar in accordance with the invention interoperates with the taper at the distal end of the sleeve of the cannula in order to further reduce the force required for insertion and at the same time smoothly bring about a friction fit of the cannula to secure it within the incision.

There is further provided a valve cap that provides sealing, and is also designed to ease insertion and removal of instruments from the cannula, by having a pre-formed pattern of one or more slits and an insertion area that utilizes the full diameter of the cannula cap. The valve cap itself is removable from the cannula and can be put on and taken off as required. An inserter is provided to ease installation of the valve cap.

The apparatus provided facilitates insertion of the trochar at a substantial incline from perpendicular. Employing this method creates a tunnel incision that closes from the normal elasticity of the sclera and the internal pressure of the eye. The tunnel incision creates a greater surface area of contact with the cannula than would a perpendicular incision, holding the cannula in place in a more secure fashion. The tunnel incision further contributes to a more rapidly healing incision.

Further features and embodiments of the invention are illustrated by the accompanying drawings and further explained in the detailed description that follows.

DETAILED DESCRIPTION

The following is a description of several preferred embodiments of various aspects of the invention. These embodiments are illustrative only. The invention is limited only by the scope of the claims that are appended hereto, and is by no means limited to particular examples described below. Further, while the examples below are shown in the context of ophthalmic surgery, the trochars described as part of the system herein are separately applicable to any other type of surgery in which trochars are employed, including without limitation cardiovascular surgery and laparoscopic surgery.

The present invention concerns a number of components that can be used independently or adapted to be used together as a system, comprising a trochar, a cannula, and elastic cannula cap and an inserted for installing the cap on the cannula. The trochar and cannula are typically made of metal, preferably stainless steel, or alternatively titanium.

In this disclosure, the least two significant digits of reference numerals are used to denote functionally corresponding but not necessarily identical structures as among various drawings. These structures will be differentiated by the leading numeral (or numerals) in the "hundreds" (or "thousands") place, and/or alternatively, by a trailing letter ("b", "d", "f", etc.) after the two least significant digits.

Careful analysis shows why the prior art trochar as described in the Background section of this specification requires greater insertion force that is optimal and leaves wounds that heal less quickly than is desirable.

Figure 2:
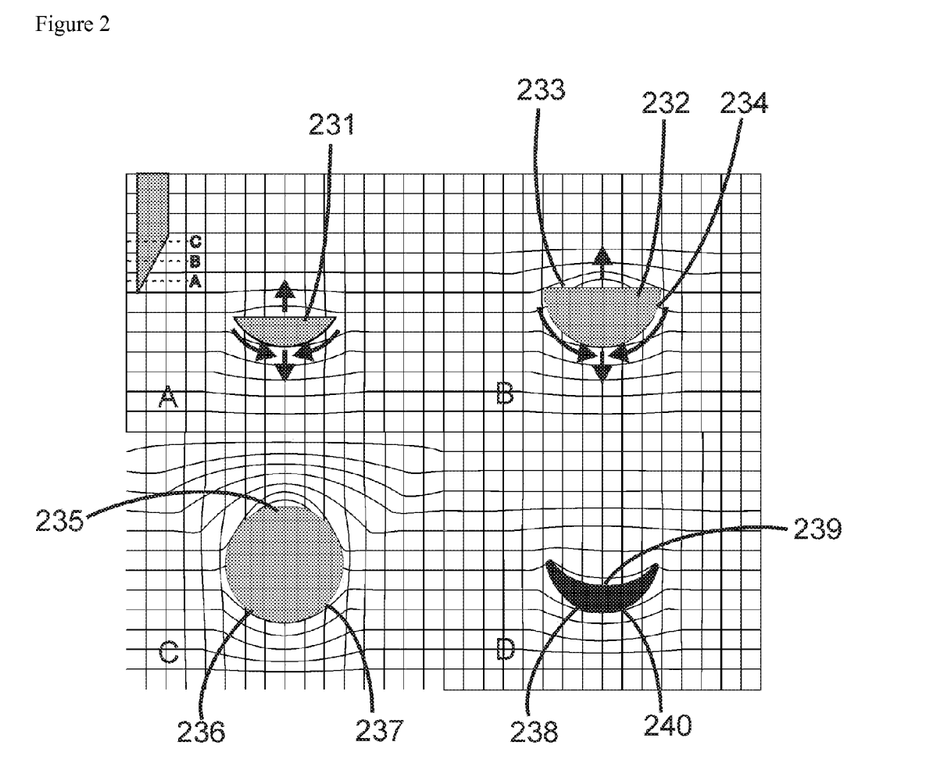
FIG. 2 is a schematic representation reflecting an analysis of the process of inserting a prior art trochar and cannula, showing the incisions at various stages of the insertion.

FIG. 2 reflects an analysis of the sizes and shapes of the incision as a trochar in accordance with the prior art, having a straight tapered edge 102, is pushed into the eye, through the sclera. When the tip at point 106 of the prior art trochar 101 first starts to incise the sclera, incision 231 is created. The tip 106 of the trochar is the sharpest point of this instrument. As the flat tapered edge 102 is further pushed into the eye, the incision expands to resemble 232. As the incision expands the curved surface on one side 234 and the flat surface on the other side 233 stretch and displace sclera tissue. As all of the straight tapered edge 102 is pushed into the eye, the edge of the trochar becomes less and less acute (and has less and less cutting efficiency) until an incision 237 having a round opening is created. The sclera around edges 235 and 236 are still being stretched. The insertion and enlargement of the incision 237 depend more on stretching and mechanical distortion of the tissue than on the cutting of the tissue. The stretching that results from the use of the prior art apparatus to insert a cannula goes beyond elastic deformation, and causes substantial irreversible plastic deformation of the sclera tissue. Thus, after the trochar and the cannula are removed from the eye, wound 240 remains on the sclera. Due to the plastic deformation of the sclera tissue, the walls 238 and 239 of the incision remain in a curved conformation, creating a "smile"—like wound pattern 240 that does not appose or heal well.

We next consider the geometry of the prior art trochar blade contour that lead to the above-described shortcomings.

First, referring again to FIG. 1, depicting a prior art trochar, the relatively obtuse angle at tip 106, and the resulting relatively large cross-sectional profile of the blade at the tip, increases the resistance offered by the eye's tissue to the penetration of the trochar. In order to overcome this increased resistance, the surgeon performing the vitrectomy surgery has to exert more force while inserting the trochar and cannula assembly. Thus when using this type of trochar there is a lot of resistance to penetration and the tapered blade section is prone to push the tissue away from the tip. This results in considerable stress and stretching at the outset, and also increases the chance that the surgeon may accidentally damage internal structures in the eye. Furthermore, as the angle between the tapered edge 102 and the round-shaped edge 103 becomes less acute, which is what occurs at the tissue surface upon insertion, the tissue around the incision is being stretched instead of being cut as the incision expands (as reflected in FIG. 2). This further stretching of the tissue of the sclera occurs after there has already been substantial stretching upon initial insertion. The overall process causes substantial plastic deformation of the tissue surrounding the incision, causing difficulty in healing and closing the incision after the vitrectomy surgery.

Second, in the prior art trochar, the angle between the flat tapered edge 102 and the rounded-shaped edge 103 is not as acute as it can be, even at the tip 106. As a general principle, as the angle of any cutting edge becomes more acute, the act of cutting becomes easier. Thus, if the angle between the tapered edge 102 and the rounded-shaped edge 103 is more obtuse than necessary, it makes the cutting action of the trochar more difficult than necessary, requiring more force to be applied, with more stretching of tissue.

Third, a round trochar, when inserted in an axial direction, will not make a cut longer than the diameter (d) of the trochar. Yet, the tissue of the sclera must eventually stretch to have a circumference approximately equal to the circumference ($\pi \times D$) of the shaft of the cannula, where (D) is slightly larger than (d). To accommodate the cannula, each edge of the cut tissue must eventually have a length approximating $\pi \times D/2$, whereas the length of the cut is (d): this represents a stretching of more than 50%. Thus, some stretching is inherent in inserting an instrument having a round profile. An advantage may be obtained by adapting the blade of such an instrument to perform more cutting and less stretching, and/or by performing the stretching, to the extent necessary, at a point in the process when it is less damaging. In that way, more of the stretching will be elastic (and reversible) and less of it will be plastic (and irreversible).

Fourth, the stretching force on the tissue is less when applied across a larger length of incision. The sequencing of cutting and stretching can affect the distribution of stretching force. In the prior art design, much stretching takes place early in insertion, when the incision is just getting started and still short, resulting in considerable initial stretching stress followed by plastic deformation.

Fifth, insertion at an angle also results in proportionately larger cut surfaces that overlap vertically, further promoting healing. In perpendicular wounds there is considerable chance the wound edges will not oppose because of interposed vitreous. When the trochar is straightened at the end of the insertion, more stretching occurs, but this is after the incision has reached maximum diameter, and when forces are therefore more distributed. Angled insertion creates a tunnel incision that closes from the normal elasticity of the sclera and the internal pressure of the eye. The tunnel incision creates a greater surface area of contact with the cannula than would a perpendicular incision, holding the cannula in place in a more secure fashion. Thus it is beneficial to perform an angled insertion. However, in order to perform an angled insertion, the length of the cutting portion of the trochar must be limited, because insertion into the sclera at an angle provides reduced clearance after insertion with respect to opposing sclera surfaces, the lens, and other intraocular structures. In an environment with limited clearance, such as the interior of the eye, a linear blade taper cannot both achieve a more acute initial blade angle and at the same time provide a blade short enough for angled insertion.

Sixth, it is desirable to make an incision slightly smaller in diameter than the diameter of the cannula in order to have a friction fit of the cannula, which will help to prevent it from falling out.

As will be seen, the present invention addresses the foregoing considerations, thereby improving the cutting action of the trochar and leaving behind a quicker- and better-healing wound.

Trochar with Curved Blade Contour

Figure 3:
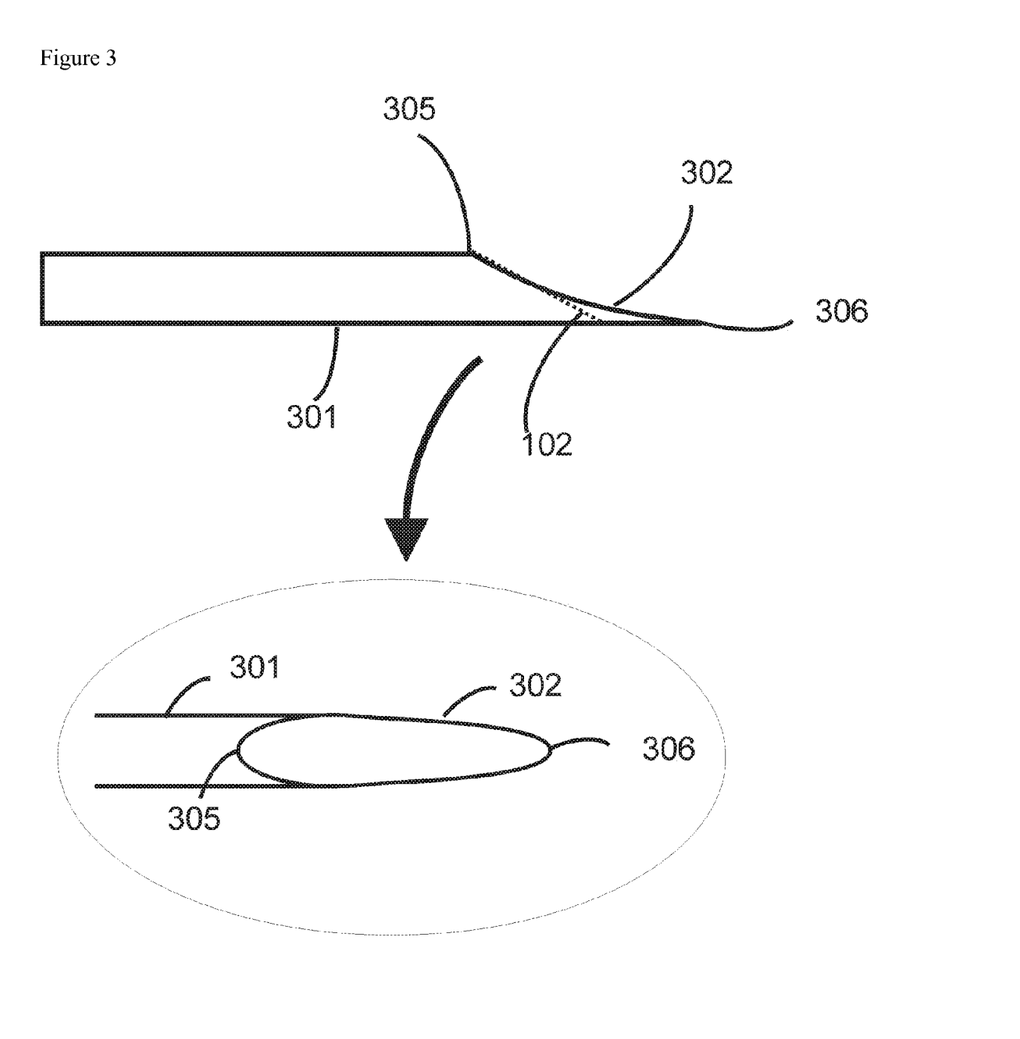
FIG. 3 shows a side section view of one embodiment of a trochar in accordance with the present invention, and an enlarged top view of the blade section of this embodiment.

In a first aspect, the present invention provides a blade cut with a curved rather than linear profile. FIG. 3 shows a comparison between the side sectional views of a prior art trochar and one embodiment of a trochar in accordance with the present invention. Whereas prior art trochar 101 has a straight tapered edge 102 at the distal end of the shaft of the trochar 101, an exemplary trochar 301 in accordance with the present invention has concavely tapered blade contour 302. The tapering starts at a first point 305, which is situated in between the proximal and distal ends of the shaft of the trochar 301. The slope at the initial portion of the curve approximates that of the straight tapered edge 102. The contour is concave, approximating parabolic, when viewed in cross-section as shown in FIG. 3. The advantage of the concave contour is that the blade near distal tip 306 is flat and thin—much flatter and thinner than is the case with a linear taper as shown in FIG. 1A. In top view, as also shown in FIG. 3, it can be seen that the tip of the blade is also narrower at the front than at the corresponding position of the linearly cut blade of FIG. 1A. The acute angle formed at distal tip 306 should be about 5 degrees or less. The sharp tip angle is also reflected in a more acute edge angle around the front side edges of the blade, whereby the entire tip area is much sharper than the tip of a prior art blade.

Because it has a more acute angle of attack, is flatter in profile, and initially narrower than the front of a prior art blade as shown in FIG. 1A, this embodiment of the present trochar blade is much sharper than the prior art blade, which is a dull and obtuse instrument by comparison. The prior art blade profile results in significant tissue stretching, requires substantial insertion force to get an incision started, and results in continuous stretching thereafter, coupled with increasingly inefficient cutting, as the trochar is further inserted. By contrast, the flat, thin leading section of the present blade serves to pilot the insertion of the trochar with clean cutting and little stretching, much more easily than the prior art blade.

With the present blade, some stretching does ultimately occur, because of the geometric factors described above. However, this stretching occurs primarily after a substantial initial opening has been cut. At that point, any necessary stretching will be distributed over a larger expanse of tissue and therefore more gentle, and mostly elastic.

A further advantage of a concave blade contour is that it can provide a degree of sharpness at the front of the blade that could only be matched by a much longer linear-tapered blade. Using a curved blade contour, in addition to its other benefits, allows the blade section to remain relatively short, even with an extremely acute and sharp initial angle of blade attack. This permits the a trochar in accordance with the invention to be inserted at an oblique angle relative to the sclera surface, thereby providing the additional benefits discussed above. In order to facilitate angled insertion, as will be discussed below, the length of the blade section of the trochar should be in the range of 3-4 mm. and preferably about 3.5 mm.

Figure 10:
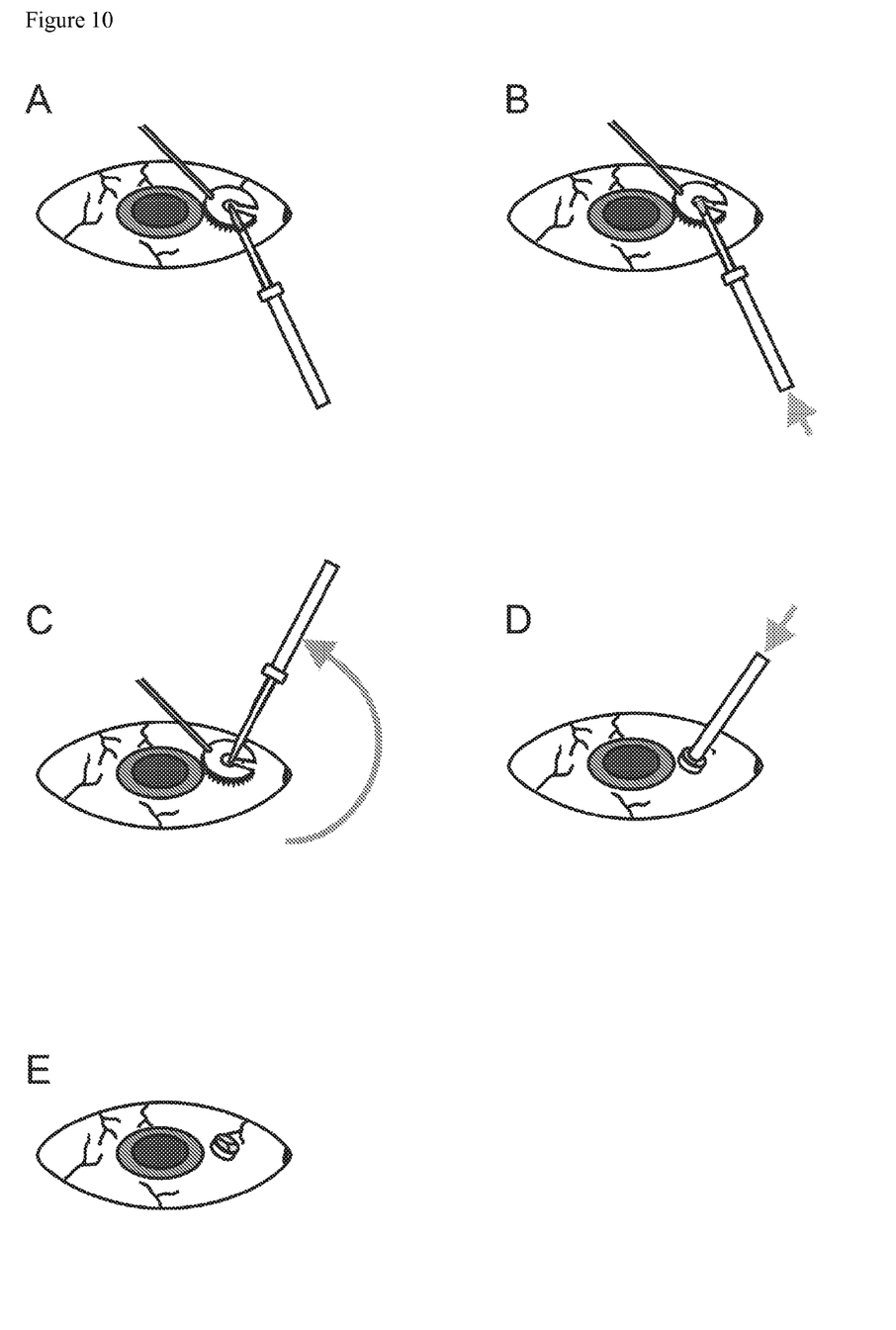
FIGS. 10A-E comprise a series of schematic illustrations depicting a method for inserting an insertion cannula in accordance with one embodiment of the invention.

A prior art trochar requires much force to insert into the eye and therefore is inserted perpendicularly. By contrast, a trochar in accordance with the invention requires much less insertion force and can be inserted at a substantial incline to the surface of the sclera, which provides considerable advantages, as discussed above. In practice, the preferred method is to hold a guide, having a central opening, on the surface of the sclera, as shown in FIG. 10A; to hold the trochar, ground blade surface up, with a cannula mounted (optionally with an elastic cap), near the opening in the guide and at approximately a 45-60 degree angle from perpendicular (also shown in FIG. 10A); to insert the assembly at this angle until the entire blade section has been inserted (FIG. 10B), and then to rotate the assembly into a perpendicular position (FIG. 10C) and insert the cannula so that its top resets upright and perpendicular on the sclera (FIG. 10D); and then, holding the cannula in place (FIG. 10E) withdrawing the trochar.

Figure 4:
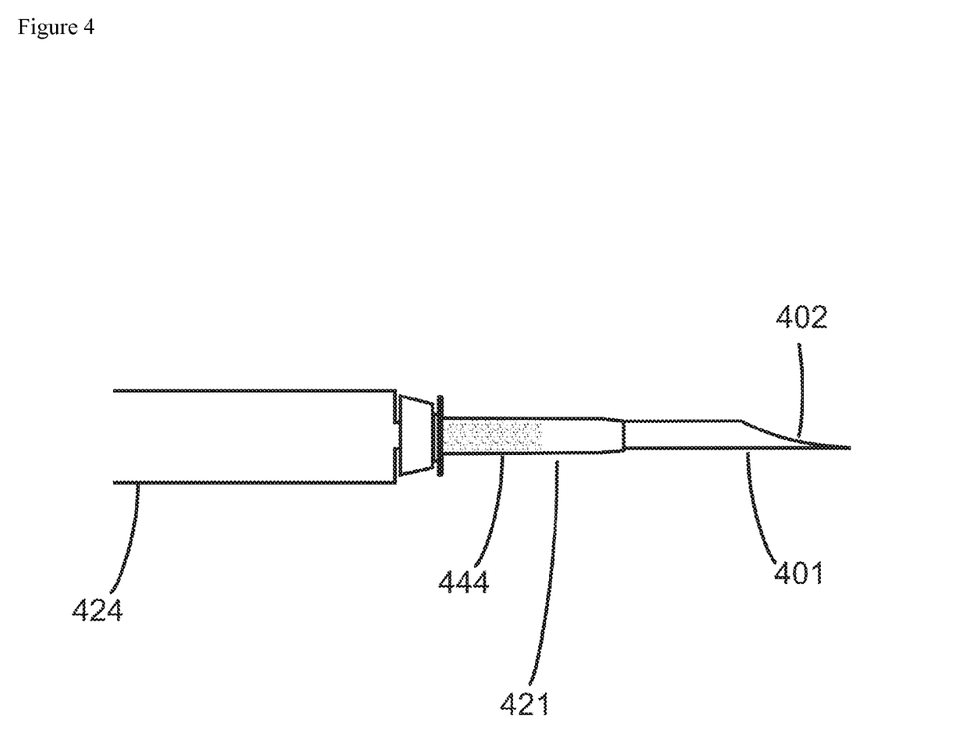
FIG. 4 is a side elevation view of another embodiment of a trochar in accordance with the present invention, showing its attachment to a handle and having a cannula mounted for insertion.

FIG. 4 is a side view of another embodiment of a trochar 401 in accordance with the present invention, showing the curved blade contour 402, the attachment to the trochar to a handle 424, and having a cannula 421 mounted for insertion. This figure also reflects that the shaft of the trochar 401 and distal portion of the cannula sleeve 422 are polished, to promote smooth insertion, and that the proximal portion 444 of the cannula sleeve has a rough surface, to promote a friction fit. (This particular illustration does not show an elastic cap.)

Optionally, a trochar having the features described above can be further improved by further reducing the blade profile. This feature is next described.

Figure 5:
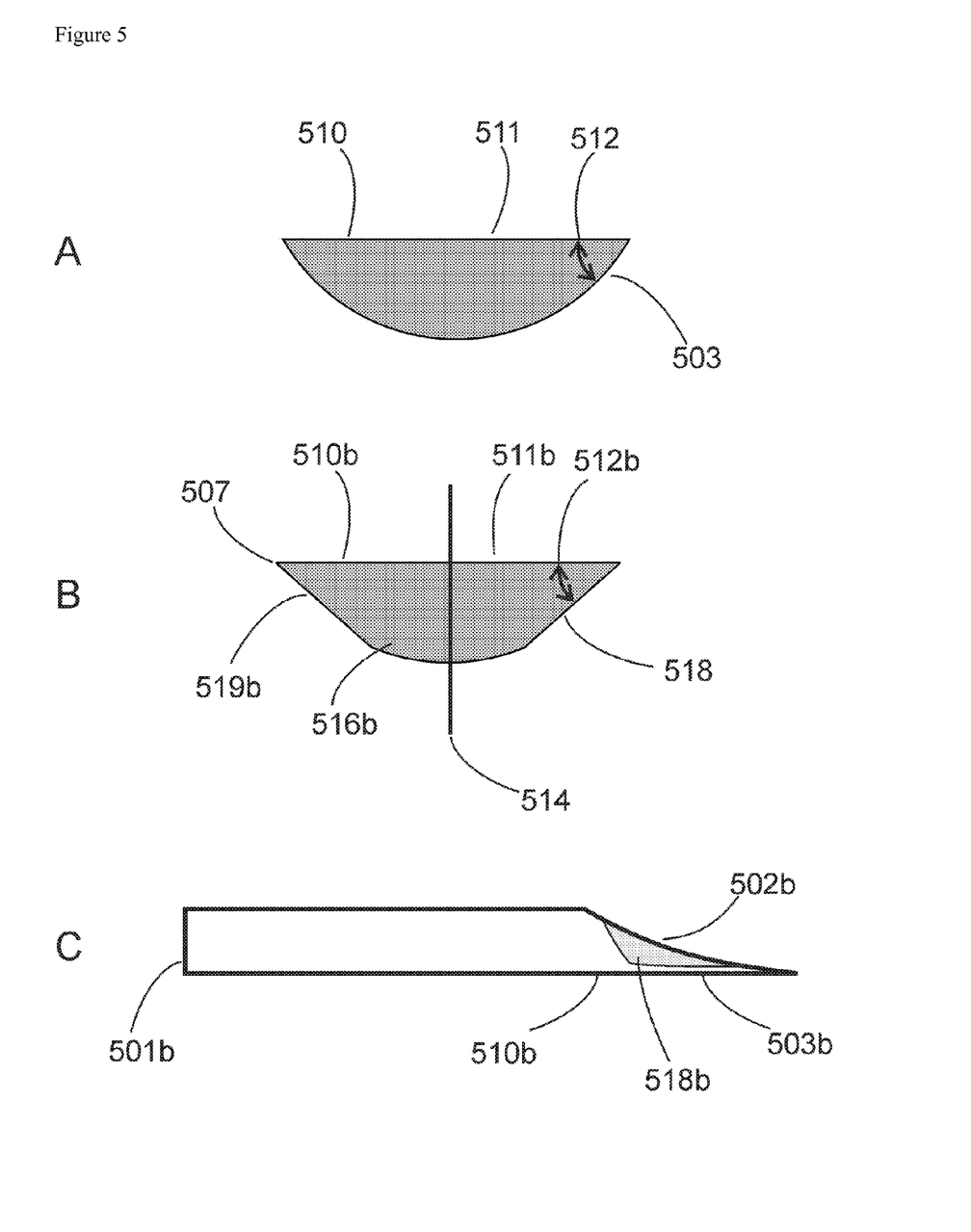
FIGS. 5A-C are two front cross-sectional views taken perpendicular to the trochar axis comparing two embodiments of a trochar blade profile, and a side elevation view further illustrating the second of those embodiments.

FIG. 5A shows a cross section, taken perpendicular to the axis, of the blade section of a prior art trochar as shown in FIG. 1A. 511 represents the flat surface of the blade section of the trochar. Curved bottom side 503 in this cross-sectional view corresponds to exterior rounded-shaped side 503 of the trochar, opposite of edge 511. Side 503 is curved in this figure due to the cylindrical shape of the trochar. As previously noted, as the angle of any cutting edge becomes more acute, cutting tends to become easier. However, the angle, 512, between the surfaces 511 and 503 will necessarily become less acute as the depth of insertion increases. In this regard, the angle 512, by becoming larger and more obtuse, can tend to make cutting of the sclera more difficult than might be otherwise the case.

FIG. 5B shows an improvement in the blade design that addresses this issue. It should be understood that the improvement in FIG. 5B may be made independent of whether a curved blade profile is also used. We assume for purposes of illustration that both the curved blade profile and the improvement about to be shown will be used in combination, and therefore an embodiment reflecting the combination of these features is the embodiment that is illustrated.

In particular, FIG. 5B shows a cross section, corresponding to FIG. 5A, of the tapered blade section of a trochar in accordance with said improvement, again as viewed axially with respect to the shaft of the trochar. Surface 511$b$ in FIG. 5B represents the curvedly ground surface of blade section 510. An imaginary longitudinally oriented plane 514 is shown that bisects the trochar axially and is normal to the edge 511$b$. Laterally disposed with respect to this imaginary plane 514 are exterior sides 518$b$ and 519$b$ running along the length of blade section 510$b$. The exterior sides 518$b$ and 519$b$ are recessed, for example, by undercutting, so that the cross-sectional area 516$b$ is smaller than that (516) of the prior art trochar. The portions of the shaft removed have no useful function and only makes angle 512$b$ more obtuse than necessary, and the blade section of the trochar thicker than necessary. As can be seen, the sides 518$b$ and 519$b$ meet surface 511$b$ to create angles 512$b$ that are more acute than angle 512. This results in better cutting action and greater ease of use of the trochar. FIG. 5C shows a side view of the trochar shown in cross section in FIG. 5B, where the trochar blade section 510$b$ has a concave contoured tapering 502$b$ that meets the side 518$b$, thus creating the more acute angles 512$b$ shown in FIG. 5B.

Cannula Design

The improvements described above in a trochar can be combined to advantage with modified designs for the cannula and valve cap. These will next be described.

First, the trochar and cannula assembly can be designed to further ease insertion, as well as to take advantage of the observation, noted above, that it is preferable to cut an incision of slightly less diameter than the cannula in order to promote a friction fit of the cannula in the sclera.

Figure 6:
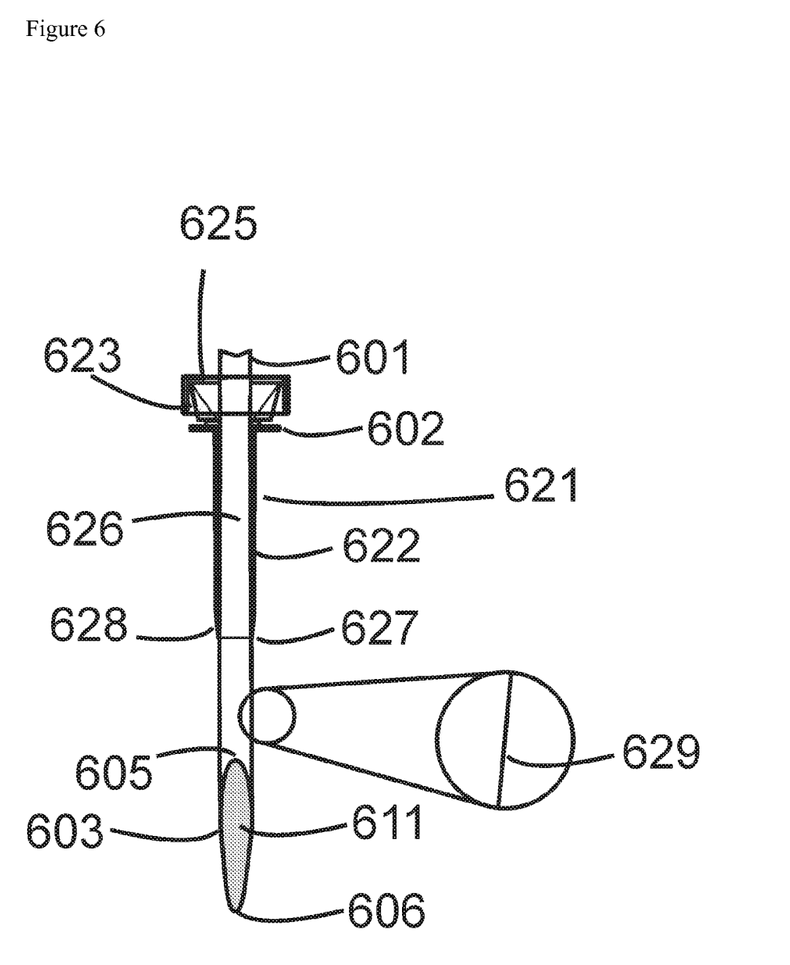
FIG. 6 shows a partially sectional view of a an exemplary trochar in accordance with the present invention, coupled with a cannula with a tubular sleeve, and a magnified view with an exaggerated depiction of the slight diametric taper on the shaft of the trochar in this embodiment.

FIG. 6 shows a side, partially sectional view of an embodiment of a trochar in accordance with the present invention, coupled with a cannula 621. In this figure, trochar 601 is inserted into the tubular sleeve 622 of cannula 621. Cannula 621 is shown in cross section so that the shaft of the trochar can be visible. Cannula 621 has a distal end 627 for insertion into the sclera (or other tissue) and a proximal end that remains on the exterior of the tissue when the cannula is inserted. At the proximal end, cannula 602 has a top section 623 adapted to receive a removable, pliable cap 625. A tubular sleeve 622 having a diameter less than that of top section 623 is attached to the distal end of the top section 623. The tubular sleeve 622 defines an opening 626 that extends through the top section 623 so that the trochar can be inserted. The distal end of the trochar 601 is extended beyond the distal end 627 of the cannula. The trochar 601 further has a sharp tip 606 created by a concave contoured tapering of surface 611. The tubular sleeve 622 has a tapered portion 628 on its exterior surface at the distal end 627 of said tubular sleeve. Tapered portion 628 creates a smooth and approximately continuous increase in diameter at distal end 627 where a junction is formed between the shaft of the trochar 601 and tubular sleeve 622, thus minimizing the transition in diameter when the distal end 627 of the cannula is first introduced to the sclera, which in turn minimizes the difficulty in inserting the cannula 621 into the sclera. As shown (in exaggerated form) in the close-up view in FIG. 6, the portion of the shaft of the trochar 601 that extends beyond the distal end 627 of the tubular sleeve 622 also, in this embodiment, has a slight taper 629. In this embodiment, the slight taper 629 starts from a point approximately adjacent to where the distal end of the shaft of the trochar 601 extends beyond the distal end 627 of the tubular sleeve, toward first point 605. Alternatively, slight taper 611 can extend to sharp tip 308. This slight taper 629 can be arranged to provide a mutual tapering with tapering 628 of the cannula tubular sleeve 622, which also further serves to minimize the transition in diameter from the outer surface of the shaft of the trochar 601 to the outer surface of the tubular sleeve 622 when the distal end 627 of the cannula is first introduced to the sclera. A further effect of having such a taper is that the blade will cut a diameter that is slightly less than the trochar diameter at the widest point of the blade, due to the above-described taper. Due to the mutual tapering in this embodiment, this friction fit may be obtained by a smooth movement.

Preferably, the friction fit of the cannula may be enhanced by slightly roughening the proximal portion of the surface of the tubular sleeve 622, as reflected by area 444 in the proximal portion of tubular sleeve 422 in the embodiment shown in FIG. 4.

Biplanar Trochar Embodiment

Figure 7:
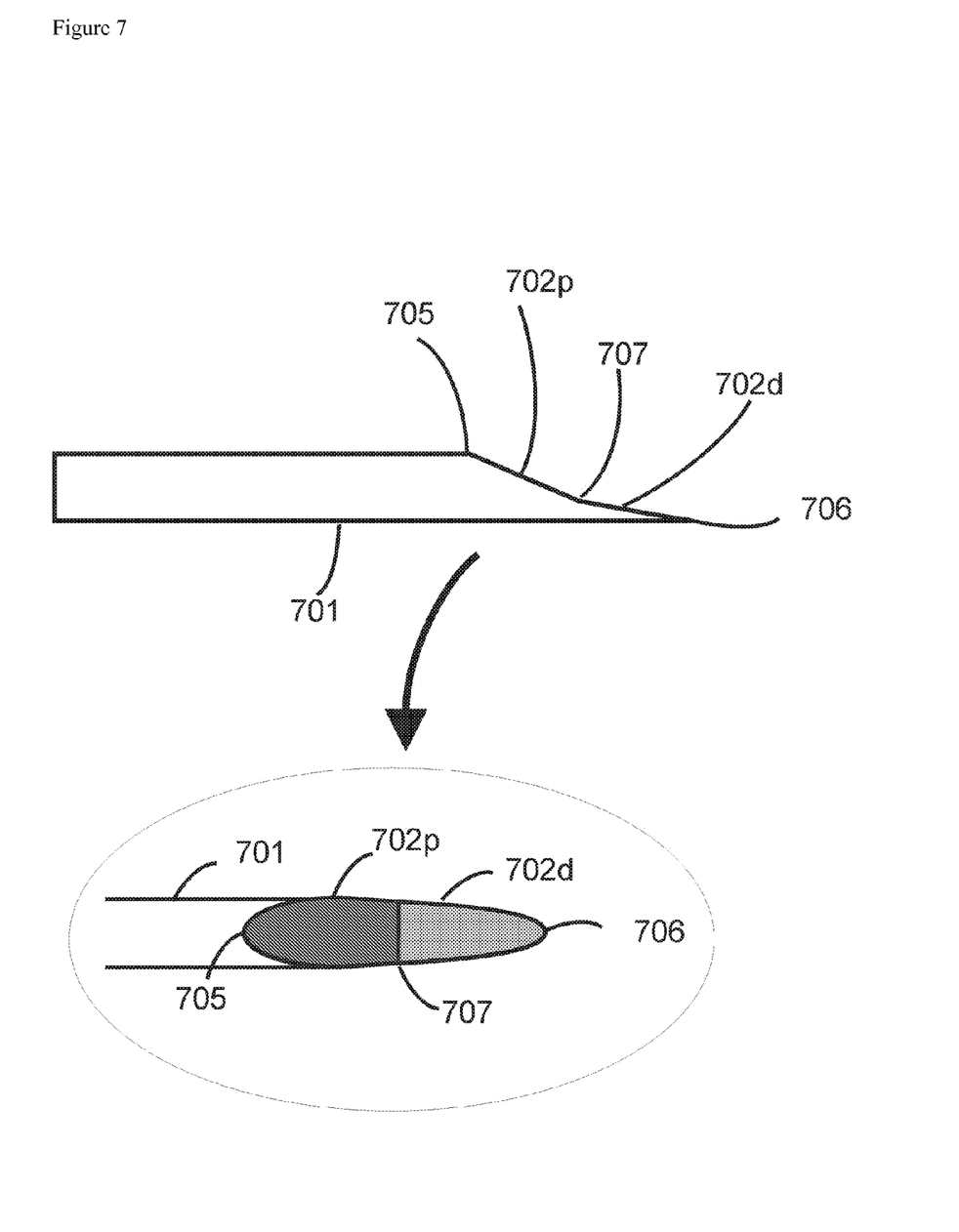
FIG. 7 is a side sectional view of another embodiment of a trochar in accordance with the invention, and an enlarged top view of the blade section of this embodiment.

FIG. 7 shows another embodiment of a blade section of a trochar, in the blade tapering 702, instead of forming a continuous curve, is divided into two adjoining linear sections, a distal section 702d and a proximal section 702p. Linear sections 702d and 702p have different angles with respect to wall 703 and meet at point (actually a line across the blade face) 707. A top view of this blade section embodiment is also shown in FIG. 7.

The trochar using the design shown in FIG. 7 is advantageous over the prior art because linear section 702d creates an angle with respect to the opposite surface 703 of the trochar shaft that is more acute and thus sharper than the cutting edge of the prior art trochar, providing for an easier initial insertion and a relatively broad initial blade cut without tissue stretching. While the acute cutting angle of distal linear blade section 702d is for those reasons advantageous, the entire blade section cannot be cut at this linear angle, because then the blade would be too long for a surgeon to operate safely. Such an elongated trochar tip could inadvertently injure structures in the eye, especially with an angled insertion technique. Thus, a second, less acute (and therefore shorter) blade section 702p follows distal blade section 702d. After distal blade section 702d creates an initial incision in the sclera tissue, the proximal section 702p, which provides a less acute angle, enlarges the incision in the sclera to allow passage of the shaft of the trochar. The combination creates an opening sufficient to fit the cannula, yet, avoiding excessive plastic deformation of the sclera tissue, for reasons similar to those discussed in connection with the curved contour blade embodiment. Indeed, the biplanar blade of this embodiment approximates in some respects the features of a curved contour design, but with linear blade sections. A person of ordinary skill in the art will recognize that proximal blade section 702p could be further divided into a series of additional linear segments of increasing angle, in a similar manner, to a similar effect.

Valve Cap Design and Inserter

Ordinarily the eye is pressurized with fluid during surgery. For each surgery two or more cannulae are placed in the eye. When instruments are in the eye, each cannula is occluded by the shaft of the surgical instrument. This prevents outflow of fluid. When the instrument is removed fluid has free access to leave the eye. Since the fluid is coming into the eye under pressure, it leaves the eye, oftentimes with a forceful stream. Excessive flow of fluid in the eye can cause damage to intraocular structures, particularly the lens of the eye. For most surgical procedures the need to replace instruments is limited, so the fluid egress from the eye is not a problem. During more complicated surgery surgical instruments need to be replaced often and excessive flow of fluid can prove to increase surgical morbidity. The need for a valve cap varies on the application and circumstances, so it is preferable that the valve cap design provide a cap whose use is optional and that can be applied and removed during a procedure as needed.

FIGS. 8A-D show an embodiment of a cap 825 in accordance with the invention, having a valvular mechanism that can be placed on the cannula to control fluid out-flow when instruments are removed from and/or interchanged in a cannula. This cap has also been designed to reduce the force that is required in order to insert and remove instruments from the cannula.

Figure 8:
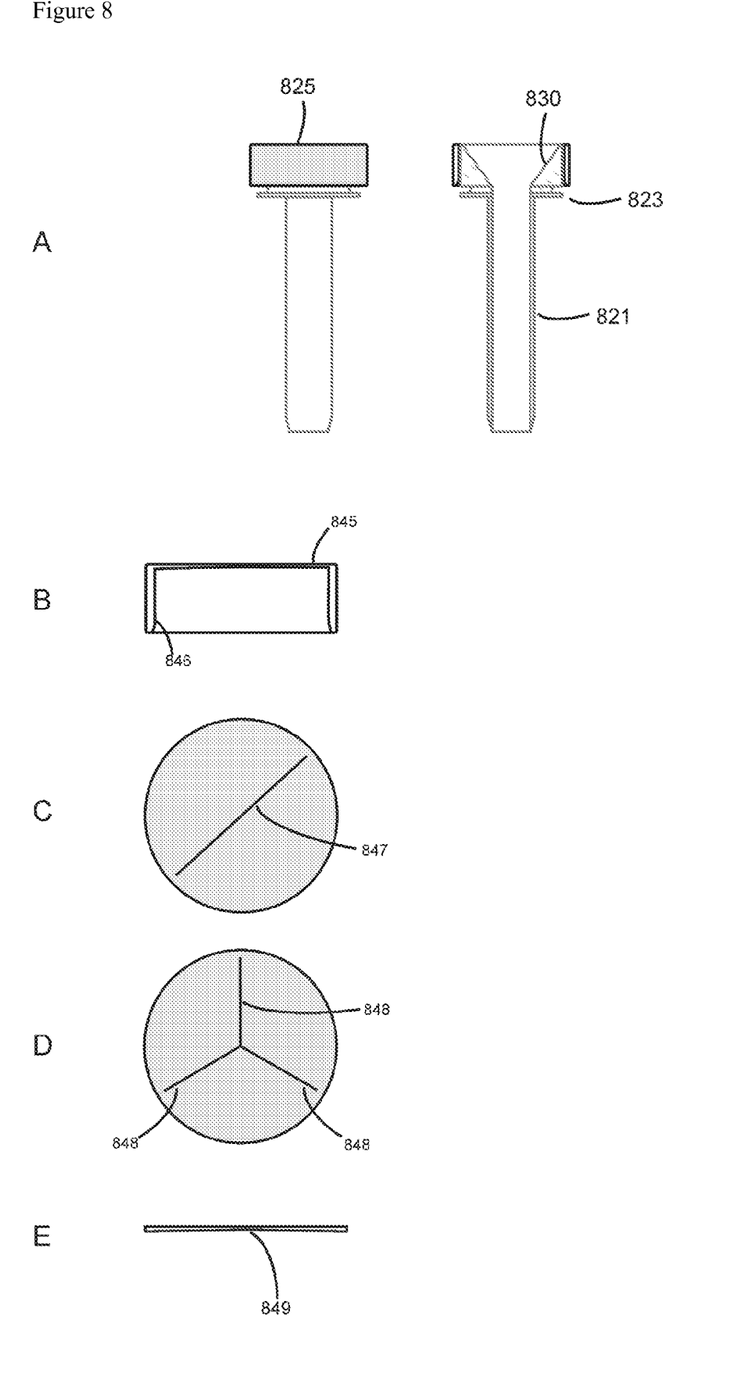
FIG. 8A shows elevation and sectional views of a cannula with a valve cap.
FIG. 8B shows is a sectional view of one embodiment of a valve cap.
FIG. 8C shows a plan view of the cap embodiment shown in FIG. 8B.
FIG. 8D is a plan view of the presently preferred embodiment of a valve cap.
FIG. 8E is an enlarged sectional view of the embodiment of a valve cap shown in FIGS. 8B and C.

Preferably, cap 825 is made from flexible inert silicone elastomer. It is a round cap with a thin upper surface 845 that becomes progressively thinner toward the center, as shown in FIG. 8B. The cap has a flared inner edge 846 at the bottom to allow easier insertion on the cannula. The cap fits snuggly on the cannula. Yet, it can easily be removed without disturbing the cannula, and is not necessary if the procedure will not require capping. Further, the cap can be applied if necessary to a cannula already in place.

Cannula 821 preferably has a funnel-shaped (or otherwise reducing diameter) cross-section 830 in the cap area, which both facilitates insertion of instruments and provides a wide diameter through which instruments may be inserted through the valve cap.

In one embodiment, the cap has a linear cut 847 made to allow instruments to be introduced into the cannula, as shown in FIG. 8C. The linear cut may be made at an angle 849, as shown in FIG. 8E, to help provide a watertight seal.

In another, more preferred embodiment, the cap has three intersecting linear cuts 848, as shown in FIG. 8D. These cuts extend diametrically across the majority of the diameter of the proximal end of the cannula cap 825. The combination of the three cuts, and their size and positioning, reduce the force required for insertion and removal of instruments into and out of the cannula. The cuts are preferably preformed in the cap, so as to provide a consistent and reliable interface.

Valve caps in accordance with the above design have the further advantage that they can be put on if needed and taken off if that is required. Moreover, it is not necessary to use them for every cannula.

Figure 9:
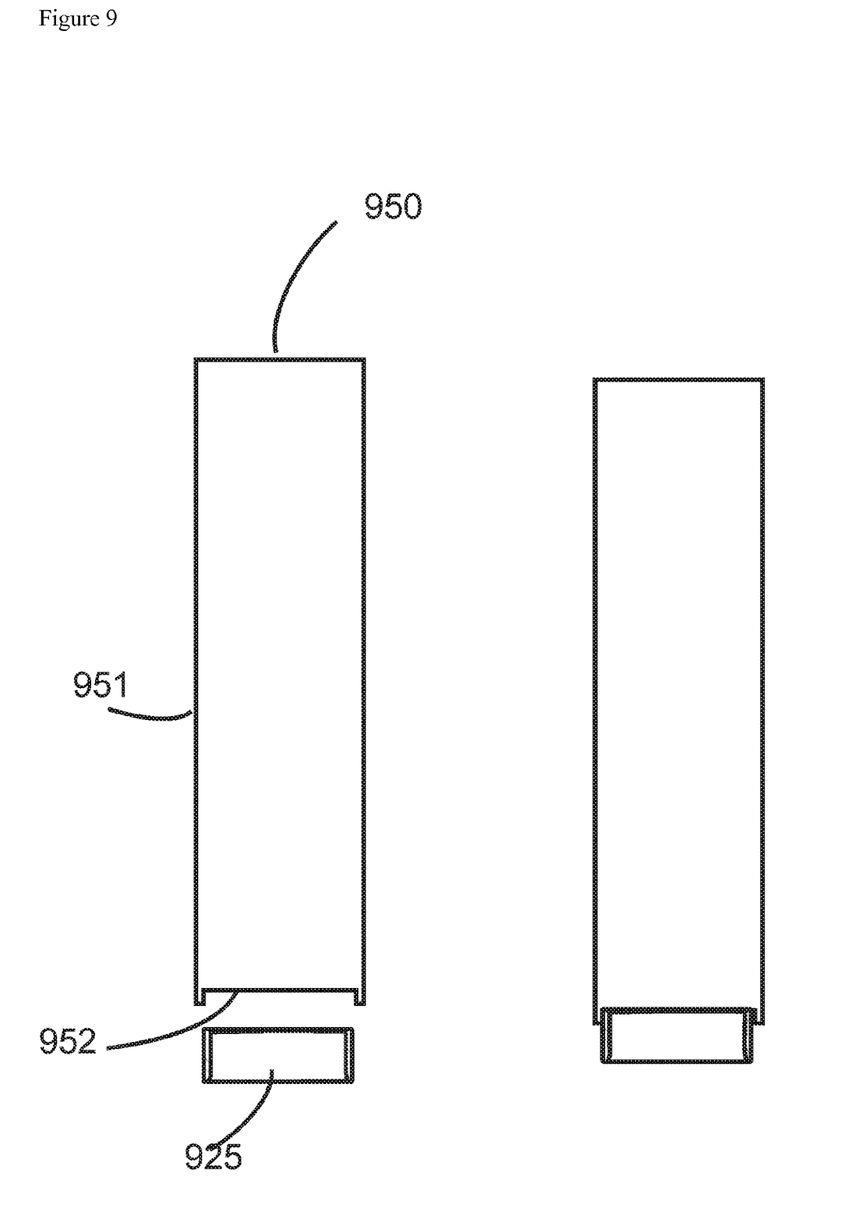
FIG. 9 shows sectional views of an inserter for a valve cap, showing the valve cap both engaged and disengaged from the inserter.

Application of the cannula cap is facilitated by an inserter 950 in FIG. 9, which comprises a cylindrical rod 951 with an opening at the bottom 952 machined to receive the cannula cap 925 and hold it securely for insertion on the top section 823 of cannula 821. FIG. 9 shows the inserter 950 with the valve cap 925 disengaged and engaged.

Absent an inserter such as described above, it would be necessary, in order to apply a cannula cap to an in-place cannula during surgery, to use one hand to hold a forceps to stabilize the cannula, and the other to hold the cap with a second forceps. Inserter 950 eases the application of a cannula cap during surgery. The cannula cap may be placed with one hand using this inserter. Thus, as reflected in the foregoing detailed description, this disclosure has provided designs for trochars, cannulae and valve caps that may be used either individually or together as a system to provide improvements in the performance of vitrectomy surgery. Those skilled in the art will recognize that there are numerous variations on each of the trochar, cannula, valve cap and inserter designs disclosed herein, and on the interoperation of all of those components, that will be within the scope of principles, objectives and solutions set forth this disclosure.

The foregoing summary, drawings, and detailed descriptions describe various embodiments of the invention and the principles by which the invention operates, and show the advantages that the invention provides over previous solutions. It is believed that the invention has been explained in sufficient detail to enable persons of ordinary skill in the field who study this disclosure to practice the techniques shown, as well as other variations and embodiments within the spirit of the invention that suit their individual needs. Accordingly, the specific features of the invention are not intended to limit the scope of the invention, as defined in the following claims.

I claim:

1. A trochar for use in an ophthalmic surgical procedure for inserting of a cannula carryable on said trochar into the sclera of a subject, in an action whereby said cannula is inserted into the sclera at an inclined angle, through an initial incision made the sclera by said trochar, without first withdrawing said trochar, comprising:
    (a) a shaft having a first boundary surface and a second diametrically opposed boundary surface defining a thickness of the shaft therebetween, the shaft having a solid cross-section extending across the thickness of the shaft, and a proximal end and a distal end configured to slidably receive said cannula thereon, such that the distal end of said shaft extends beyond said cannula when said cannula is fully received on said shaft for insertion; and
    (b) a tapered blade section at the distal end of said shaft, beginning at a first point situated distally beyond the distal end of said cannula when said cannula is fully received on said shaft for insertion, coming to a sharp tip further defining an acute angle at the most distal portion of said shaft of no greater than about 5 degrees, wherein said blade section, measured from said tip to said first point is about 3-4 mm in length;
    said trochar being usable to perform said insertion without substantial plastic deformation of sclera tissue.

2. The trochar of claim 1 wherein said contour has a concave curved shape with respect to a linear line extending from said first point to said tip.

3. The trochar of claim 1 wherein the length of the blade section is about 3.5 mm.

4. The trochar of claim 1 wherein said blade section comprises a first subsection and a second subsection, said first subsection having a linear contour and being situated at the distal end of said blade section, and said second subsection section being proximal of first subsection, adjoining said first subsection, and generally disposed at an angle less acute with respect to the lengthwise opposing exterior surface of said shaft than that of said first subsection.

5. The trochar of claim 4 wherein said second subsection also comprises a linear blade subsection so as to provide a biplanar blade section.

6. The trochar of claim 1, wherein the exterior sides of said shaft distal of said first point, opposite said contour, and laterally disposed with respect to the longitudinally oriented plane normal to said contour, are recessed so as to reduce the cross-sectional area of said tapered blade section as viewed axially with respect to said shaft.

7. The trochar of claim 1, wherein said shaft is made of metal.

8. The trochar of claim 7, wherein said metal is selected from the group comprising stainless steel and titanium.

* * * * *